United States Patent
Uri et al.

(10) Patent No.: US 10,359,397 B2
(45) Date of Patent: Jul. 23, 2019

(54) HORIZONTAL ELECTROPHORESIS SEPARATION DEVICE WITHOUT SEAL AND METHOD OF EXTRACTING GEL WITHOUT OPENING CASSETTE

(71) Applicant: Bio-Rad Laboratories, Inc., Hercules, CA (US)

(72) Inventors: Yochanan Uri, Givat Ela (IL); Uri Issman, Haifa (IL); Igor Kochetkov, Afula (IL); Itay Barak, Haifa (IL); Shai Aharon, Yokneam Illit (IL); Shai Nimri, Kibutz Nir David (IL)

(73) Assignee: Bio-Rad Laboratories, Inc., Hercules, CA (US)

( * ) Notice: Subject to any disclaimer, the term of this patent is extended or adjusted under 35 U.S.C. 154(b) by 457 days.

(21) Appl. No.: 14/968,400

(22) Filed: Dec. 14, 2015

(65) Prior Publication Data

US 2016/0299099 A1  Oct. 13, 2016

Related U.S. Application Data

(60) Provisional application No. 62/092,731, filed on Dec. 16, 2014.

(51) Int. Cl.
G01N 27/447 (2006.01)
G01N 33/543 (2006.01)

(52) U.S. Cl.
CPC . *G01N 27/44756* (2013.01); *G01N 27/44726* (2013.01); *G01N 27/44739* (2013.01); *G01N 27/44743* (2013.01); *G01N 27/44782* (2013.01); *G01N 33/54366* (2013.01); *G01N 27/44721* (2013.01)

(58) Field of Classification Search
CPC .............. G01N 27/447; G01N 27/26; G01N 27/44769; B01L 2400/0415; B01L 2400/0421; B01L 3/502753; C07K 1/26; C07K 1/28
See application file for complete search history.

(56) References Cited

U.S. PATENT DOCUMENTS

| 4,279,361 | A | * | 7/1981 | Chung | ............... B01L 99/00 222/1 |
| 5,259,943 | A | * | 11/1993 | Kozulic | ......... G01N 27/44704 204/616 |
| 5,338,426 | A |  | 8/1994 | Shigeura et al. | |

(Continued)

OTHER PUBLICATIONS

International Search Report and Written Opinion dated Apr. 8, 2016 in PCT/US2015/065571, 19 pages.

(Continued)

*Primary Examiner* — Gurpreet Kaur
(74) *Attorney, Agent, or Firm* — Kilpatrick Townsend and Stockton LLP

(57) ABSTRACT

Horizontal gel electrophoresis devices and methods of extracting a gel from a gel housing are provided. The devices allow for extraction of gels without having to open the housing comprising the gel. The devices include gel cassettes that simplify the automation of gel electrophoresis and electroblotting of proteins. Also provided are devices that allow for horizontal gel electrophoresis without the need to from a liquid seal between the buffer reservoir and the gel housing. Also described are methods for extracting a gel from a housing without opening the housing.

11 Claims, 7 Drawing Sheets

(56) References Cited

U.S. PATENT DOCUMENTS

| | | | |
|---|---|---|---|
| 5,433,837 A * | 7/1995 | Brunk | G01N 27/44704 |
| | | | 204/620 |
| 6,576,109 B1 | 6/2003 | Hsu | |
| 6,682,641 B1 | 1/2004 | Finney et al. | |
| 2003/0132117 A1 | 7/2003 | Guttman et al. | |
| 2003/0221962 A1 | 12/2003 | Ingenhoven et al. | |
| 2004/0091943 A1 | 5/2004 | Schneider | |
| 2006/0266649 A1 | 11/2006 | Nakamura et al. | |
| 2008/0047834 A1 | 2/2008 | Park et al. | |
| 2010/0326830 A1 | 12/2010 | Wang | |
| 2011/0042213 A1 | 2/2011 | Updyke et al. | |

OTHER PUBLICATIONS

Partial Supplemental European Search Report in PCT/US2015/065571 dated Jul. 16, 2018; 14 pages.

* cited by examiner

HORIZONTAL ELECTROPHORESIS SEPARATION DEVICE WITHOUT SEAL AND METHOD OF EXTRACTING GEL WITHOUT OPENING CASSETTE

The present application claims the benefit of priority to U.S. Provisional Application No. 62/092,731, filed Dec. 16, 2014, which is incorporated by reference herein in its entirety.

BACKGROUND OF THE INVENTION

Polyacrylamide gel electrophoresis (PAGE) is a useful technique for analyzing biological macromolecules such as proteins or nucleic acids. PAGE separates biological molecules based on their electrophoretic mobility, which is a function of the charge, size, and conformation of the molecule. Biological molecules can be analyzed in their native conformation or denatured such that the molecule's mobility through the gel matrix is a function of its length (i.e., size) and its mass-to-charge ratio. A common denaturant for proteins is sodium dodecyl sulfate (SDS), an anionic detergent that linearizes and adds a negative charge to the protein molecule. When SDS is added to the protein sample for gel electrophoresis, the technique is referred to as SDS-PAGE. During PAGE, the sample containing the biological molecule(s) (e.g., analyte) of interest is loaded into a sample well at one end of the gel, and an electric filed is applied across the gel, resulting in the negatively charged analytes migrating from the cathode (negatively charged electrode) towards the anode (positively charged electrode). A dye is typically added to the gel in order to monitor the progress of electrophoresis, and visible or stain free molecular weight markers can be added to one or more sample wells to further monitor the separation of molecules by size. The electric field is removed after the user determines the analyte of interest has migrated through the gel enough to be sufficiently separated from other analytes.

If the molecule of interest is a protein, PAGE separation of the protein analyte can be followed by western analysis. In western analysis, protein analytes are typically transferred to a solid support, such as a filter or membrane (e.g., nitrocellulose or polyvinylidene difluoride (PVDF)). The proteins can be transferred to the membrane by capillary action or electroblotting. In electroblotting, the proteins in the gel are contacted with an electric field that causes the (negatively) charged proteins to migrate out of the gel toward an electrode (anode) and contact the membrane. After the protein of interest is immobilized on the surface of the membrane, the protein is contacted with an antibody (the primary antibody) that specifically binds the protein of interest. The bound antibody is then detected, for example by contacting the primary antibody with a secondary antibody conjugated to a detectable label such as biotin, HRP or AP, or a fluorescent label. The detectable label is then visualized, for example by chemiluminescence. Western analysis provides additional confirmation that a protein or analyte of interest is present in the sample loaded on the gel.

BRIEF SUMMARY OF THE INVENTION

The present disclosure describes devices and methods for horizontal gel electrophoresis. In one aspect, a device for horizontal gel electrophoresis is provided, the device comprising:
 a first and second chamber for holding buffer, the first and second chamber separated from each other and each comprising a floor, wherein the floor of the first and second chamber each comprises one or more opening providing fluid communication between the first and second chambers and one or more separation channel; the separation channel(s) residing below the floor of the first and second chambers; and
 a cathode disposed within the first chamber and an anode disposed within the second chamber.

In some embodiments, the openings in the floor of at least one of the first and second chambers form sample wells that protrude above the surface of the floor such that a volume of sample can be contained in each well. One or more separation channel(s) can comprise an electrophoresis gel, for example, a polyacrylamide gel. In some embodiments, the separation channels each have a first and second end, the first end of said separation channels abutting an extrusion member capable of sliding to extrude the electrophoresis gel in the separation channel out of the second end of the separation channel. In some cases, the device further comprises a track aligned with each separation channel to receive a gel extruded by the extrusion member from the separation channel. To provide an electric field to transfer analytes out of the electrophoresis gel, the device can further comprise a first transfer electrode positioned above the track that is configured to receive the extruded gel, and a second transfer electrode positioned below the track. The track can be part of or disposed in a solid support comprising pores and a medium for conducting ions.

In some embodiments, the bottom and/or the top of the separation channel comprises a transparent material that facilitates visual monitoring of the separation of analytes in the gel. The device can comprise a plurality of separation channels, e.g., at least 5 separation channels, or from 10 to 24 separation channels.

In some embodiments, the first and second chamber are separated from each other by a dividing wall. In some embodiments, the first and second chamber are horizontally separated from each other such that at least a portion of the separation channel is visible between the first and second chambers. The floor of the first and/or second chamber can comprise a transparent material, or the separation channel can comprise a transparent material. In some embodiments, the first and/or second chamber further comprises an inlet and an outlet configured to circulate buffer by way of a pump that flows buffer from the inlet to the outlet.

In a second aspect, a device for horizontal gel electrophoresis is provided, the device comprising:
 a first chamber for holding buffer comprising a floor, wherein the floor of the first chamber comprises one or more opening providing fluid communication between the first chamber and one or more separation channel; the separation channel(s) residing below the floor of the first chamber; and
 a cathode disposed within the first chamber.

In some embodiments, the openings in the floor of the first chamber forms sample wells that protrude above the surface of the floor such that a volume of sample can be contained in each well. One or more separation channel(s) can comprise an electrophoresis gel, for example, a polyacrylamide gel.

In some cases, the separation channels each have a first and second end, and can further comprise an extrusion member in slidable contact with the electrophoresis gel at the first end of the separation channel, wherein the extrusion member is configured to slidably extrude the electrophoresis gel in the separation channel out of the second end of the separation channel. In some embodiments, the extrusion member is slidably disposed within an extrusion member channel aligned with a longitudinal axis of the separation channels.

The device can further comprise a second chamber for holding buffer and, In some embodiments, an anode disposed with the second chamber. In some cases, the second chamber configured to removably receive the first chamber. In some embodiments, the second chamber comprises one or more tracks aligned with the one or more separation channels to receive a gel extruded by the extrusion member from the separation channel. The one or more tracks can be submersed in a buffer added to the second chamber.

In a third aspect, a device for horizontal gel electrophoresis is provided, the device comprising:
  a first and second chamber for holding buffer,
    each of said chambers composed of a floor, two side walls, an outer wall, an inner wall, and a dividing wall, said dividing wall separating an inner portion and an outer portion of the chamber, said dividing wall having one or more dividing wall openings to allow for buffer flow between said inner and outer portions,
    each of the chambers configured to circulate buffer between said inner and outer portions, and
    each chamber comprising an electrode;
  disposed between, and attached to, the inner walls of said first and second chambers, one or more platform for receiving a horizontal gel housing, wherein the dividing wall openings horizontally align with a gel in the gel housing, if present, such that buffer in the chambers can contact the gel, if present, and pass from the inner portions to the outer portions.

In some embodiments, the outer walls of the chambers have one or more outer wall openings that horizontally align with the one or more dividing wall openings. The outer wall openings can further comprise a removable cover.

In the above aspects, the first and/or second chamber can comprise an inner and outer portion separated by a dividing wall. The dividing wall can have openings to allow for buffer flow between the inner and outer portions of the chamber(s). The inner and outer portions of the chambers can comprise at least one of an outlet and an inlet, and the chambers are configured to circulate buffer between said inner and outer portions by way of a pump that flows buffer from the inlet to the outlet with buffer returning via the dividing wall openings. In some embodiments, said inlet is in the inner portion and said outlet is in said outer portion of the chamber.

In some embodiments, the device further comprises a horizontal gel housing. The horizontal gel housing can comprise a top and a bottom, wherein the bottom rests on the one or more platform, and the top comprises one or more barrier to prevent buffer from flowing from one chamber to another of said chambers. In some embodiments, the horizontal gel housing further comprises a cross-linked gel.

In a fourth aspect, a method of extracting an electrophoresis gel from a housing without opening the housing is described, the method comprising:
  providing a housing containing the gel, the housing comprising open first and second ends, wherein the gel is exposed at the first end and second end;
  contacting the exposed gel at the first end with an extrusion member with sufficient force to push the gel out of the second end of the housing, thereby extracting the gel from the housing.

In some embodiments of the method, the gel and the extrusion member have similar cross-sectional shapes. The gel can be a cross-linked gel. In some cases, the housing comprises one or more gel electrophoresis channels, and the gel is contacted at a first end of the channel with the extrusion member with sufficient force to push the gel out of a second end of the channel. In some embodiments, the method further comprises contacting the extruded gel with an electric field to transfer an analyte in the gel to a solid support. In some cases, the method further comprises identifying a characteristic of the analyte.

In a fifth aspect, a method for analyzing an analyte following gel electrophoresis is provided, the method comprising:
  extruding a gel comprising analytes separated by size or charge from a separation channel of a device described herein onto a track aligned with the separation channel;
  contacting the extruded gel with an electric field between first and second transfer electrodes such that the analytes are electrophoretically transferred to a solid support; and
  analyzing the analyte.

In some embodiments of the method, the analyte is a protein and analyzing comprises contacting the protein with an antibody that specifically binds the protein, and detecting the bound antibody.

In some embodiments, the gel is extruded by contacting the gel with an extrusion member with sufficient force to push the gel out of the separation channel onto the track. In some cases, the gel is extruded by vibrating the device of claim 1 under conditions suitable for extruding the gel from the separation channel onto the track.

In a sixth aspect, a method for aligning an image of a gel is described, the method comprising:
  comparing a first image of a gel prior to extrusion of the gel from a gel housing to a second image of the gel after extrusion from the gel housing;
  determining if a reference band in the first image is shifted relative to the reference band the second image;
  aligning the first image and the second image based on the position of the reference band before the gel is extruded.

In a seventh aspect, a system for aligning images of a gel is provided, the system comprising:
  a device comprising an electrophoresis gel comprising a dye band;
  a detector capable of detecting the dye band;
  a computer configured with executable instructions for aligning a first image of the gel and a second image of the gel,
  wherein the first image is obtained before the gel is extruded from a gel housing, and the second image is obtained after the gel is extruded from the gel housing, and the images are aligned based on the position of the dye band before the gel is extruded.

BRIEF DESCRIPTION OF THE DRAWINGS

FIG. 4A shows a perspective view. FIG. 4B shows a top view of the embodiment shown in FIG. 4A.

FIG. 5A shows a top perspective view showing one exterior side, an exterior end, and the removable gel carrier housing of the horizontal gel box; FIG. 5B shows a top view; and FIG. 5C shows a cut-away view along section B-B.

DEFINITIONS

Figure 1:
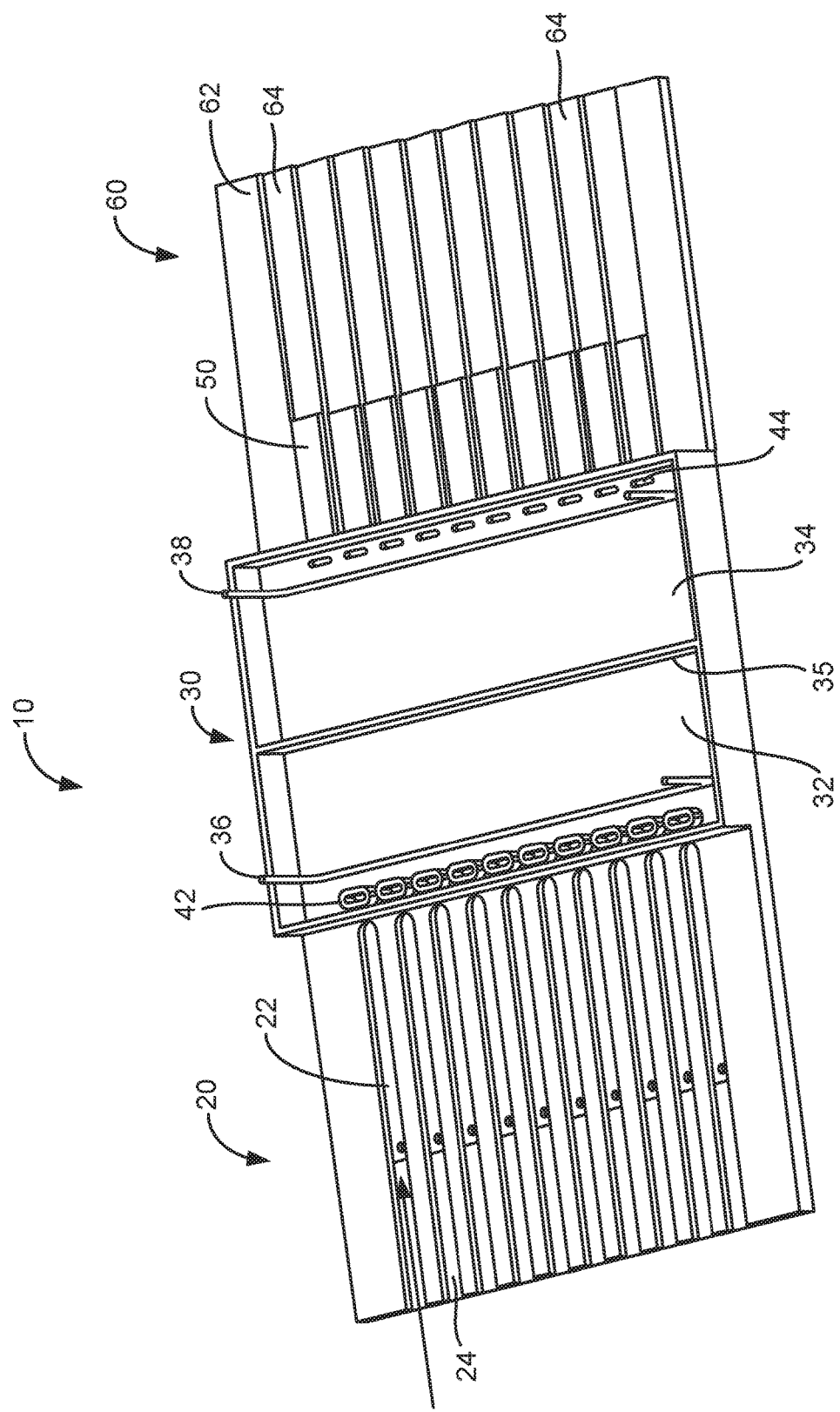
FIG. 1 shows a perspective view of one embodiment of a gel cassette described herein.

The term "separation channel" refers to a gel electrophoresis channel configured to separate analytes (e.g., proteins) by size and/or electric charge. The channel can contain a preloaded electrophoresis gel, such as a polyacrylamide gel. Alternatively, the gel can be added to the channel by a user prior to separating the analytes.

The term "fluid communication" and grammatical equivalents refers to the potential for a fluid, such as a liquid or buffer, to flow or move between two points. If the fluid is a buffer comprising ions, or a gel that does not substantially move, the term also includes the term "electrical communication," and grammatical equivalents, such that an electric current can flow between two points. Thus, the term includes instances where the fluid may not flow, but an electric current can pass through the fluid.

The term "gel" refers to a material suitable for separating molecules by size (molecular weight or mass), charge and/or conformation. The term includes gels comprising a matrix of agarose, polyacrylamide, or starch. The gels described herein are suitable for analyzing nucleic acids and proteins.

The term "about" refers to values that are within 1-10% of a numeric value provided herein, e.g., with plus or minus 1%, 2%, 3%, 4%, 5%, 6%, 7%, 8%, 9%, or 10% of a value.

DETAILED DESCRIPTION OF THE INVENTION

Described herein are devices and methods for gel electrophoresis. The devices and methods facilitate the automation of analyzing analytes by gel electrophoresis. The device allows electrophoretic separation of analytes such as proteins in a horizontal configuration without the need for a physical seal between the gel housing and the buffer reservoirs, thereby making it simpler to automate the process of analyzing analytes. The device can also comprise a gel extraction cassette that simplifies the automation of analyzing analytes, for example, by western blot (also referred to as protein immunoblot) analysis. The devices described herein are also useful for analyzing nucleic acids, for example, by Southern analysis. The methods allow for extracting a gel from a housing without having to open the housing to extract the gel, which also makes it simpler for automation of the process.

Gel Extraction Cassette

In one embodiment, the device is a cassette for horizontal gel electrophoresis that is useful for analyzing analytes such as proteins or nucleic acids. In some embodiments, the cassette is useful for automating the analysis of proteins by western analysis. In some embodiments, the device is a disposable cassette.

In some embodiments, the device comprises a separation section comprising first and second chambers for holding a buffer. The first and second chambers comprise a floor, and the floor of each chamber comprises one or more openings that are in fluid communication with one or more separation channels. The separation channels reside below the floor of the first and second chambers. In some embodiments, the device comprises a plurality of separation channels that are aligned next to each other below the floor of the chambers. In some embodiments, the device comprises at least 5, or from about 5-50, about 5-40, about 10-30, or about 10-25 separation channels. In some embodiments, the device comprises 5, 6, 7, 8, 9, 10, 11, 12, 13, 14, 15, 16, 17, 18, 19, 20, 21, 22, 23, 24, or 25, 30, 35, 40, 45, or 50 separation channels.

Each chamber further comprises an electrode, for example, a cathode can be disposed in the first chamber and an anode disposed in the second chamber. The first and second chambers are spatially separated from each other, but can be electrically coupled by a gel matrix (described below) in the separation channel. In some embodiments, the first and second chambers are separated from each other by a dividing wall. In some embodiments, the first and second chambers are horizontally separated from each other, such that at least a portion of the separation channel residing below the floor of the chambers is visible from above. In some embodiments, the floor and/or the separation channel comprises a transparent material (e.g., transparent PVC, Lustran SAN, Topas (COC) or any other transparent moldable polymer) that allows the user to visually observe the progress of the electrophoretic separation by monitoring a dye front or marker ladder. In some embodiments, the floor of the first and/or second chamber comprises the top of the separation channel(s). In some embodiments, the floor of the first and/or second chamber is the same material as the top of the separation channel(s). In some embodiments, the bottom of the separation channel is a transparent material. The device can be coupled to optical sensors (e.g., line CMOS sensor, UV absorbance sensor, etc.) or image processing systems that automatically monitor the progress of electrophoresis, for example, through the transparent floor material, and turn off the current when electrophoresis has proceeded sufficiently to adequately separate the analytes of interest.

In some embodiments, the openings in the floor of the first and/or second chambers form sample wells that protrude above the surface of the floor such that a volume of sample can be contained within each well.

In order to separate analytes such as proteins by size and/or charge, the device can further comprise an electrophoresis gel. In some embodiments, the separation channels comprise a gel, e.g., a cross-linked gel. The separation channels can be prefilled with the gel matrix material. The separation channels are electrically insulated from each other, but are open at each end such that the gel material is exposed at both ends of the channel. Both ends of each channel are in contact with the cathode and anode chambers through the one or more openings in the floor, such that the ends of the gel, when present, are in contact with buffer present in the cathode and anode chambers. Thus, the anode and cathode chambers, while not in direct fluid communication, are in electrical contact through the gel material when buffer is present in the chambers. When voltage is applied between the electrodes, the sample loaded into the sample wells migrates into the gel and is subjected to electrophoresis in the separation channel.

In some embodiments, the bottom and/or the top of the separation channels comprise a transparent material (e.g., transparent PVC or other rigid transparent material). As above, this allows the progress of the electrophoresis to be visually monitored, either manually (i.e., by human vision) or by optical or image processing equipment.

The first and/or second chambers can further comprise an inlet and an outlet configured to circulate buffer by way of a pump that flows buffer from the inlet to the outlet. In some embodiments, the buffer flows into the top of the chamber and exits via the outlet in the floor of the chamber. This configuration provides the advantage that no physical seal is required between the chambers and buffer reservoir.

In some embodiments, the cassette further comprises one or more gel extrusion members. The gel extrusion member can be a plunger or piston-like device that is elongated along one axis. In some embodiments, the gel extrusion members are disposed in a housing that is attached or integral to the cassette. For example, the housing comprising the extrusion members can be disposed adjacent to the floor of the cathode chamber of the separation section. The housing can further comprise tracks or channels for aligning the gel extrusion members with the long-axis of the separation channels (e.g., with the lumen of the separation channels). In some embodiments, the separation channels each have a first end and a second end, and the first end abuts or contacts an extrusion member. The extrusion member is configured to slidably contact the electrophoresis gel in the separation channel in order to extrude the gel out the second end of the separation channel. The device will typically comprise an equal number of separation channels and extrusion members, though other configurations are within the scope of this disclosure. In some embodiments, the device comprises at least 5 extrusion members, or from about 5-50, about 5-40, about 10-30, or about 10-25 extrusion members. In some embodiments, the device comprises 5, 6, 7, 8, 9, 10, 11, 12, 13, 14, 15, 16, 17, 18, 19, 20, 21, 22, 23, 24, or 25, 30, 35, 40, 45, or 50 extrusion members. The extrusion members can be pushed manually or by a common actuator. In some embodiments, the extrusion members are disposable. In some embodiments, the extrusion members are in contact with the gel and act as plugs to prevent the gel from falling out of the separation channels during gel casting, or from drying out during storage. The extrusion member and the gel can have similar cross-sectional shapes to ensure uniform contact with the gel material. The end of the gel opposite the extrusion member can be sealed to prevent gel dehydration during storage, and the seal removed by a user before use.

In some embodiments, the device further comprises a transfer section attached to or integral to the cassette. In some embodiments, the transfer section is attached to the anode chamber end of the device, for example, in substantially the same plane as the bottom of the separation channels. In some embodiments, the transfer section comprises a surface configured to receive the gel extruded from the separation channel by the force of the extrusion member. In some embodiments, the surface comprises one or more tracks that are aligned with the separation channels and are configured to receive the gel extruded by the extrusion member. In some embodiments, the surface is a solid support (e.g., a transfer card) comprising tracks configured to receive the gel extruded by the extrusion member. In some embodiments, the solid support comprises pores and a medium for conducting ions (e.g., a buffer). The solid support can also be made of a hydrophilic material. In some embodiments, the solid support is a porous plastic hydrophilic material (e.g., a Porex® card). In some embodiments, the solid support acts as a conductive support for the gel strips as well as an ion source for the electrophoretic transfer of analytes to a blot membrane.

In some embodiments, the transfer section of the device further comprises electrodes positioned above and below the solid support for elctrotransfer of biomolecules in the gel to a membrane or other material. For example, a first electrode (called a transfer electrode) can be positioned above the solid support, and a second transfer electrode is positioned below the solid support. In some embodiments, the anode is positioned above the solid support, and the cathode is positioned below the solid support. In this configuration, voltage applied to the electrodes results in migration of analytes out of the gel toward the anode. The analytes can thus be transferred to and immobilized on a second solid support, such as a membrane, that is suitable for further assays, such as western analysis. Thus, the extruded gel is sandwiched between the lower solid support (transfer support) and the upper, second solid support (e.g., blotting membrane). Alternatively, the cathode can be positioned above, and the anode positioned below the gel, in which case the second solid support (e.g., blotting membrane) would be positioned below the gel strips.

The cassette device can be used in combination with an instrument that provides pressure to hold the blot membrane against the gel disposed on the transfer support. For example, the instrument can comprise a frame configured to hold the blot membrane, the frame being attached to the transfer electrode. The transfer electrode can be part of a lid that is closed to apply pressure to the gel to facilitate transfer of the analytes to the second solid support. In some embodiments, the transfer electrode is attached to a spring controlled by an actuator that regulates the amount of pressure exerted on the gel.

For manufacturability purposes, the construction of the cassette may involve bonding of multiple parts. For example, the separation section of the cassette may be divided into an upper and lower part that are injection molded and later bonded together (by adhesive or chemical or ultrasonic welding or other methods known in the art) to create the inner channels. Alternatively, the inner channels may be manufactured separately by extrusion and then assembled/bonded to the bottom of the cassette to hold them together and seal against the buffer reservoir on top of it. The separation channels of the cassette may be chemically treated/coated to improve hydrophobicity and improve gel extrusion (e.g. with Silane). To improve curing of the gel, the outer face of the cassette may be coated with Serfene or other oxygen barrier layer.

The cassette described herein provides several advantages, described below:

First, the cassette has isolated separation channels that allow gel strips to be pushed out of the cassette for transfer of analytes to the second solid support. Thus, no further handling of the fragile gel material prior to transfer is required, which greatly reduces instrument complexity and the risk of damaging the gel material.

Second, the cassette design allows electrophoresis without the need for a physical fluid seal on multiple interfaces, which simplifies the instrument and improves reliability.

Third, the transparent top and/or bottom of the separation channels allows a user to visually monitor the separation process, either by the unaided human eye or by using a image analysis system.

Fourth, the position of the electrophoresis electrodes above the separation channels simplifies automation. For example, the electrodes can be mounted to the inner side of a safety lid that is closed by the user. The position of the electrodes keeps both ends of the cassette clear to allow the gel to be extruded from the separation channels.

Fifth, the conductive, porous solid support (e.g., the transfer support card) provides tracks to guide the gel strips and secures them in place while providing support and allowing electrophoretic transfer upwards.

Sixth, the position of the sample wells allows convenient sample loading either manually or automatically by conventional pipetting.

Seventh, the gel extrusion members (e.g., plungers) are an integral part of the cassette and act as plugs for the channels during casting of the gel. This omits the need for the user or instrument to remove a cover prior to use and simplifies the instrument to reduce instrument cost. It also omits the need for accurate alignment of the cassette with respect to an actuator of the gel extrusion members.

Eighth, embodiments incorporating disposable gel extrusion members are required to operate only a single time. The design of such single use operation is much less demanding than designing the gel extrusion members as part of the instrument since gradual wear over time is not a concern.

Ninth, the cassette design allows all moving parts of the instrument to be dry which greatly simplifies the instrument and improves reliability.

Tenth, the design does not require handling of multiple fine and fragile disposable components such as capillaries, and does not require loading of sieving media into capillaries.

Eleventh, the only disposable component that needs to be automatically manipulated by the instrument is the blot membrane. The cassette, the solid support (e.g., transfer card) and the transfer blotting pads can all be loaded by the user upon setting up the experiment and require no further handling.

In some embodiments, the gel is extruded by vibrating the cassette along the extrusion axis. Thus, the use of vibration to extrude the gel can result in a cassette that does not require a housing section for the gel extrusion members, further simplifying the design, improving the potential for automation and lowering the cost of manufacture. The use of vibration to extrude the gel can be applied to a slab gel or gel strips. In some embodiments, the gel is extruded by a combination of vibrating the cassette and applying pressure with the gel extrusion members.

Turning now to FIG. 1, an exemplary, non-limiting embodiment will be described. Cassette (10) comprises, from left to right, a housing section (20), a separation section (30), and a transfer section (60). The housing section (20) comprises one or more gel extrusion members (22) that can be disposed in a track or channel (24). The gel extrusion member can be a plunger or piston like device that is elongated along one axis. The long axis of the gel extrusion members is aligned with the lumen of the separation channels.

Figure 2:
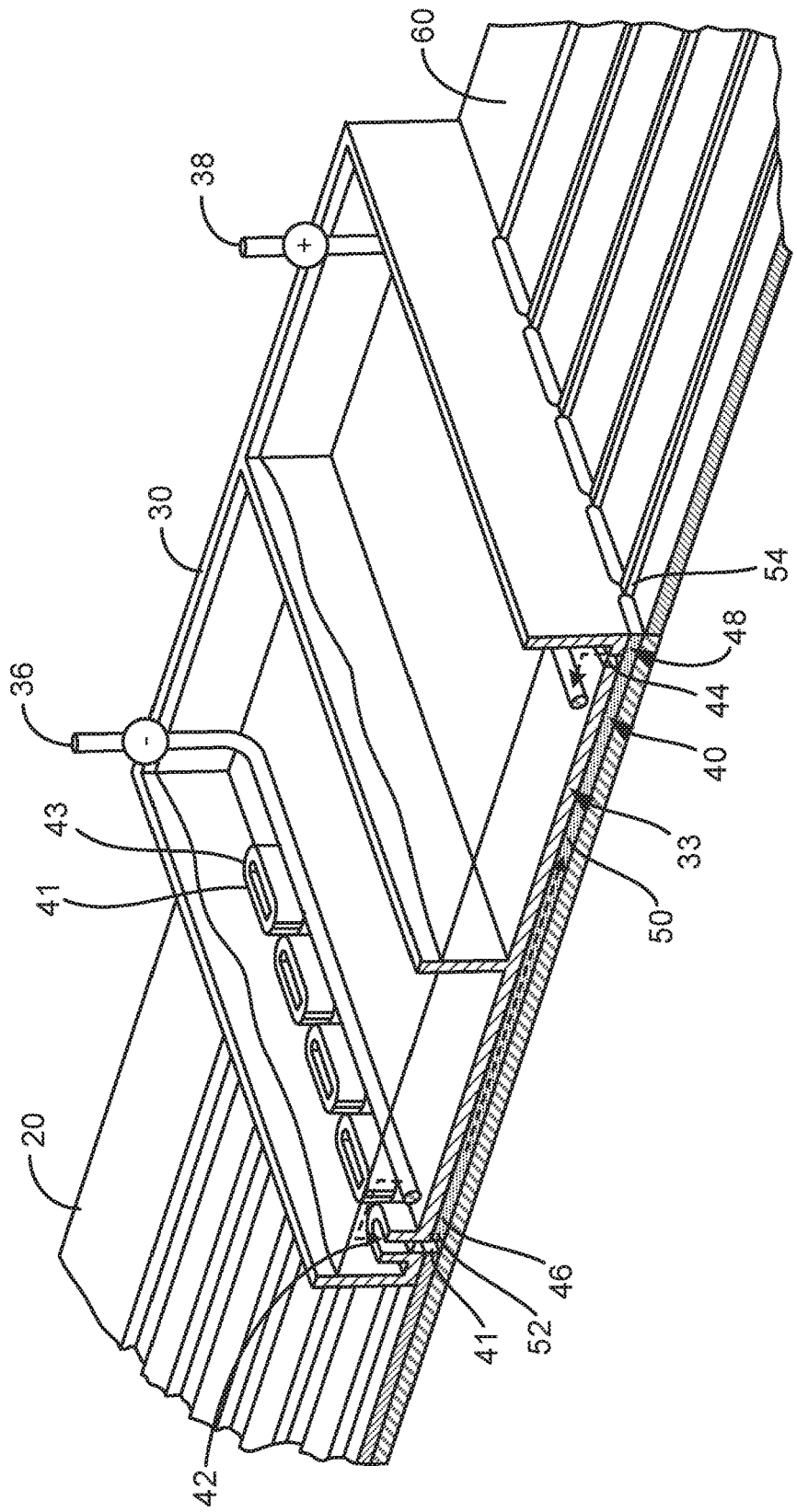
FIG. 2 shows a cut-away view of one embodiment of a gel cassette described herein.

The separation section (30) comprises a first chamber (32) and a second chamber (34). In the embodiment shown, the chambers (30, 32) are separated by a dividing wall (35); however, other configurations are possible. For example, the chambers can be separated by an extension of the floor (33) between the two chambers such that the chambers do not share a common wall. In some embodiments, the floor (33) is made of a transparent material that allows the progress of electrophoresis to be visually monitored by the (unaided) human eye or by an image processing system. The first chamber (32) includes a first electrode (36), e.g., a cathode, and the second chamber (34) includes a second electrode (38), e.g., an anode. The first and second chambers can be open at the top for receiving a buffer solution comprising ions. As shown in FIG. 2, the separation section further comprises horizontal separation channels (40) disposed below the floor (33) of the first and second chambers. The first end (46) of the separation channel is connected to a sample well (42) comprising an opening (41) in the floor of the first chamber (32). The sample well (42) has a rim or walls (43) that extend upwards from the floor (33) to reduce the risk of cross contamination between other sample wells. In use, buffer is added to the chambers such that the level of the buffer exceeds the height of the sample well rim (43) to allow buffer continuity between the cathode and the sample in the well. As shown in FIG. 1, section (30) further comprises openings (44) in the floor of the second chamber (34). The opening (44) is in fluid communication with the second end (48) of the separation channel to provide electrical continuity between separation channel and the anode (38).

The separation channel can further comprise a gel (50) that extends from the first end (46) to the second end (48). The gel is exposed at each end (52, 54). End 52 is in contact or slidably contacted with the gel extrusion member (22). End (54) is exposed at the end adjacent the transfer section (60). End (54) can be sealed with a removable seal to prevent gel dehydration during storage, and the seal is removed by the user before running the gel.

Figure 3:
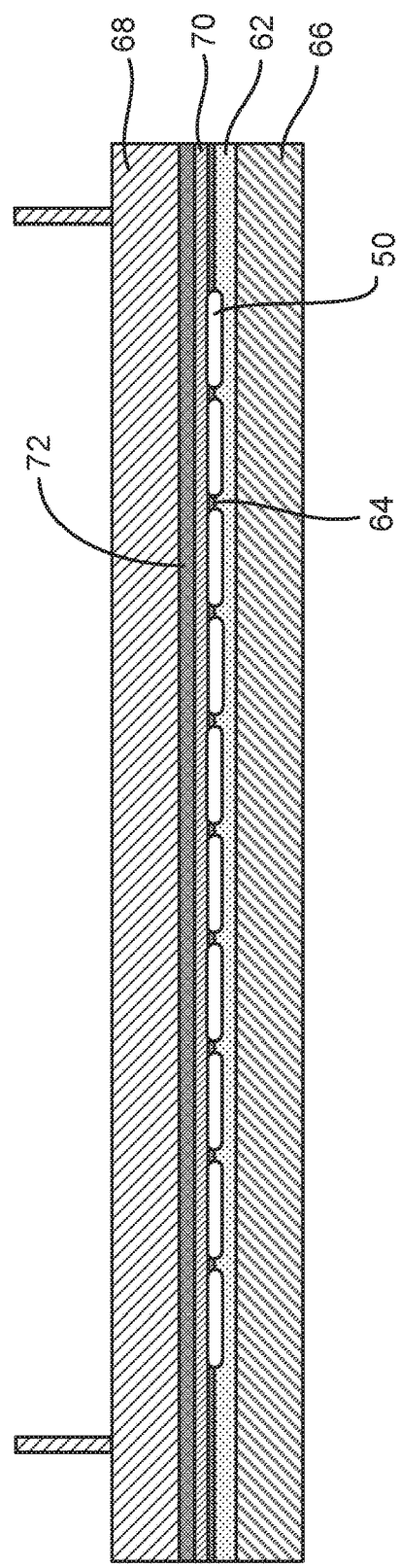
FIG. 3 shows an end view of one embodiment of a gel cassette transfer section described herein.

The transfer section (60) comprises a solid support (62). In some embodiments, the support (62) is a hydrophilic, porous polyethylene material (e.g., Porex™-4899, Porex Technologies, Atlanta, Ga.). Support (62) comprises one or more tracks (64) that are aligned with end (54) of the gel and configured to slidably receive the gel (50) extruded from the separation channels. As shown in FIG. 3, the support (62) is disposed between two electrodes, e.g., a transfer cathode (66) and a transfer anode (68). A second solid support (70), e.g., a membrane suitable for western blotting, such as a nylon membrane, is disposed between the electrodes and above the gel strips (50). If desired, pads (72) comprising a buffer can be added between support (70) and anode (68). In the configuration shown in FIG. 3, voltage applied to the electrodes results in upward migration of analytes present in the gel (toward the anode) such that the analytes contact and are immobilized on the support (70). However, other embodiments are possible. For example, filter paper or pads can be placed between electrode (66) and the support (62), and the order and arrangement of the pads and support (62) can be arranged as desired to optimize transfer of the analytes.

Figure 4A:
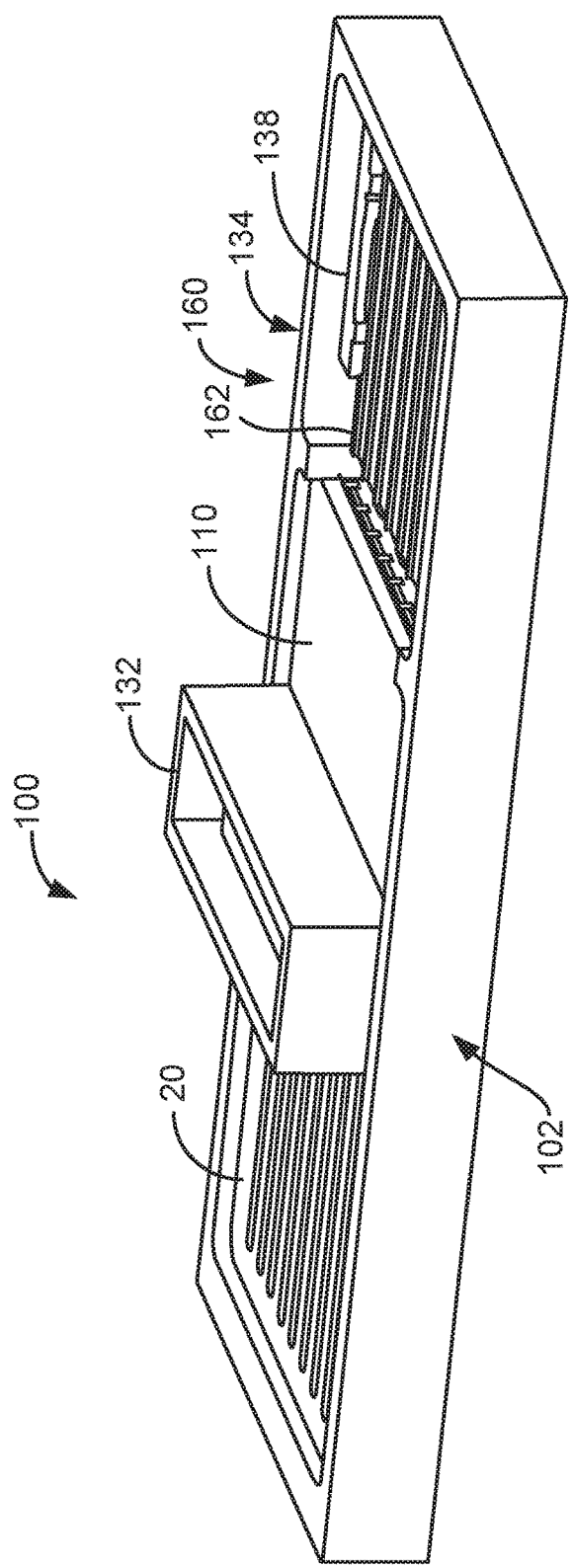
FIGS. 4A and 4B show a representative embodiment of another gel cassette described herein.
Figure 4B:
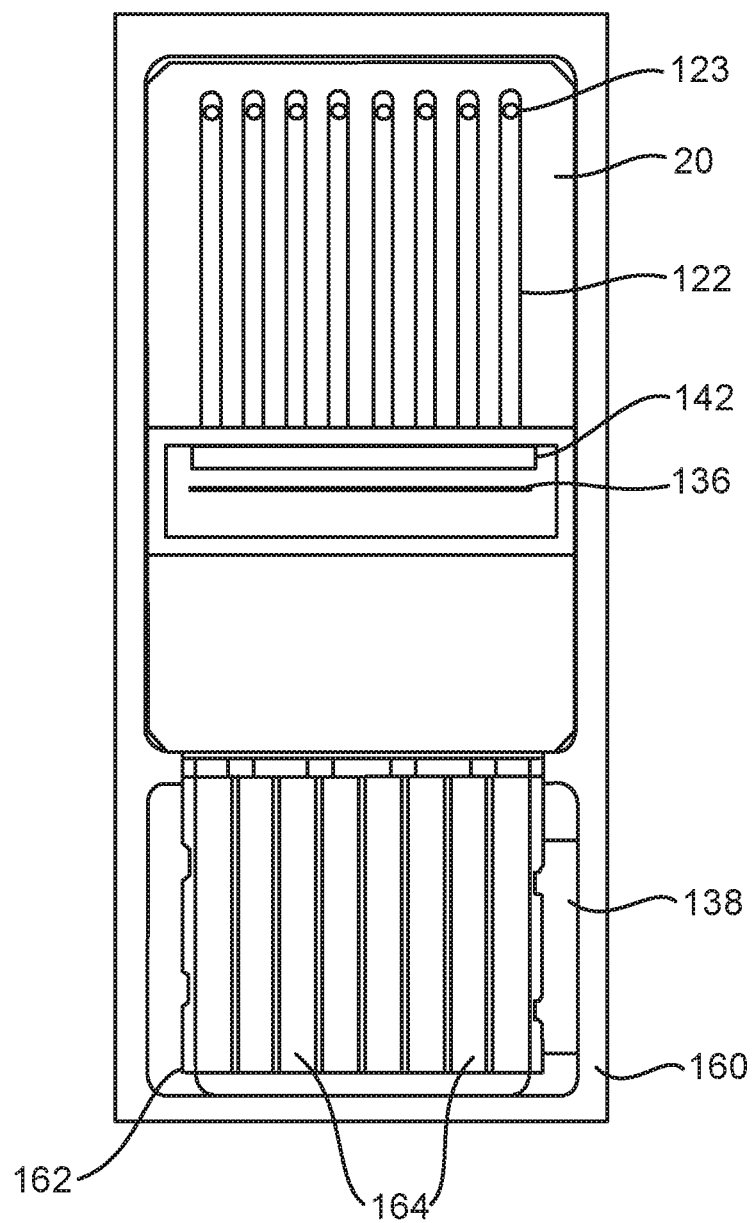

Turning now to FIG. 4, another exemplary embodiment will be described. As shown in FIG. 4A, instrument (100) comprises a chamber or tray (102) configured to receive cassette (110). In some embodiments, the chamber (102) is rectangular in shape and comprises a floor and four sides connected to the floor. At least a portion of chamber 102 can be filled with buffer to function as a bath into which cassette (110) is placed. Similar to the embodiment described in FIG. 1, the cassette comprises a cathode reservoir (132) containing a cathode (136) and sample wells (142) (FIG. 4B). However, in this embodiment, the anode (138) is disposed in the chamber (102), and therefore is in contact with any buffer added to chamber (102). Thus, in one embodiment, the chamber (102) comprises an anode reservoir (134) configured to receive the transfer section (160) of the cassette. As above, the transfer section (160) comprises a solid support (162) having tracks (164) that are aligned with the ends of the gel strips (50). In operation, the anode reservoir (134) is filled with buffer, thereby submerging solid support (162). The presence of buffer reduces the friction between the gel strips and the solid support as the gel strips are extruded from the separation channels by the gel extrusion members (122).

In some embodiments, the gel extrusion members (122) are connected to an actuator (not shown) configured to provide sufficient force to push the gel strips out of the separation channels. For example, in one embodiment, the end (123) of the gel extrusion member that is distal to the separation channels is connected to an actuator arm that is connected to an actuator device. In the embodiment shown in FIG. 4A, the gel extrusion members (122) are disposed in channels or lanes (not shown). In some embodiments, the channels or lanes configured to receive the gel extrusion members (122) are about 8 mm wide, about 1 mm deep, and about 70 mm long. In some embodiments, the cassette (110) is made of transparent PVC, which allows for proper curing of the polyacrylamide gel due to its low oxygen permeability.

Horizontal Electrophoresis Device without Seal

In another aspect, a horizontal electrophoresis device is provided, where the device does not require a seal between the buffer reservoirs and the gel housing. Thus, the device configuration makes it simpler for automation. In some embodiments, the device comprises two chambers (i.e., a first and second chamber) for holding buffer, where each chamber comprises a floor, two side walls, an outer wall, an inner wall, and a dividing wall. The dividing wall separates each chamber into two subchambers (e.g., an inner chamber portion and an outer chamber portion) that are in fluid communication with each other. In some embodiments, the dividing wall comprises one or more openings to allow buffer to flow between the inner chamber portion and the outer chamber portion. The one or more openings are typically located near the top of the dividing wall, such that in operation, the buffer fills most of the inner chamber portion before flowing through the openings into the outer chamber portion.

Each chamber further comprises an electrode. In some embodiments, the electrode is located in the inner chamber portion. In some embodiments, the electrode is located in the outer chamber portion.

In some embodiments, each of the chambers is configured to circulate buffer between the inner and outer chamber portions. For example, the buffer can be circulated by a pump that is in fluid connection with the inner and outer chamber portions. In some embodiments, the inner and outer chamber portions comprise an inlet and an outlet for circulating buffer. For example, the inner chamber portion can have an inlet in fluid connection with a pump and the outer chamber portion can have an outlet in fluid connection with a pump, or vice versa (i.e., the inner chamber portion can comprise the outlet and the outer chamber portion can comprise the inlet, both in fluid connection with a pump). In some embodiments, the buffer flows from the inlet to the outlet with buffer returning via the divided wall openings. In some embodiments, the buffer flows from the inner chamber portion to the outer chamber portion, or vice versa. In some embodiments, the buffer flows from the inner chamber portion to the outer chamber portion via the one or more openings in the dividing wall. In some embodiments, the dividing wall does not comprise openings, and the buffer flows over the dividing wall from the inner chamber portion to the outer chamber portion.

In some embodiments, the outer walls of the chambers comprise one or more outer wall openings that are horizontally aligned with the one or more dividing wall openings. For example, the dividing wall and the outer wall can each comprise from 1 to 24 openings, e.g., 1, 2, 3, 4, 5, 6, 7, 8, 9, 10, 11, 12, 13, 14, 15, 16, 17, 18, 19, 20, 21, 22, 23, or 24 openings. The outer wall openings can further comprise a removable cover that prevent buffer from exiting the chamber.

In some embodiments, the chambers are further configured to receive a horizontal gel housing that extends from the first chamber to the second chamber. For example, in some embodiments, the chambers can comprise one or more platforms that support the horizontal gel housing. The platform can be attached to the inner wall of the first and second chambers, such that the platform is disposed between the inner walls of the first and second chambers. The horizontal gel housing can comprise a gel that is exposed at each end of the housing. In some embodiments, the openings in the dividing wall are horizontally aligned with the gel in the housing when the housing is present. This allows the buffer in the chambers to contact the gel, if present, and flow from the inner chamber portion to the outer chamber portion.

In some embodiments, the device further comprises the horizontal gel housing. The horizontal gel housing comprises a top and a bottom, and first and second ends. In some embodiments, the bottom of the gel housing rests on the one or more platforms. In some embodiments, the top of the gel housing comprises one or more barriers to prevent buffer from flowing out of the chamber, for example, from one chamber to the other chamber. The barrier serves to keep the buffer in each chamber separated from the buffer in the other chamber. In some embodiments, the gel housing comprises a gel. In some embodiments, the gel is a cross-linked gel. The gel housing is open at the first and second ends so that the gel is exposed. In some embodiments, the gel housing comprises a plurality of openings at each end that are aligned with the openings in the dividing wall. The number of openings in the gel housing can be the same number of openings in the dividing wall, for example, from 1 to 24 openings, e.g., 1, 2, 3, 4, 5, 6, 7, 8, 9, 10, 11, 12, 13, 14, 15, 16, 17, 18, 19, 20, 21, 22, 23, or 24 openings.

In operation, as the buffer flows from the inlet to the outlet, it contacts the end of the gel in the gel housing. Thus, the buffer in the first chamber contacts the gel exposed at the first end of the gel housing, and the buffer in the second chamber contacts the gel exposed at the second end of the gel housing. The flow of buffer creates electrical continuity between the electrodes and the gel. In some embodiments, the buffer enters the chamber portion comprising the electrode and contacts the gel in the housing to create buffer and electrical continuity between the electrode and the gel. After contacting the gel, the buffer flows into the chamber portion comprising the outlet and is recirculated back to the inlet. In some embodiments, the buffer flows over or through the one or more openings in the dividing wall and enters the outlet chamber portion. In some embodiments, the buffer flows under and/or over the gel housing and is circulated to the outlet. The barriers on the gel housing prevent the buffer from exiting the first and second chambers.

Figure 5A:
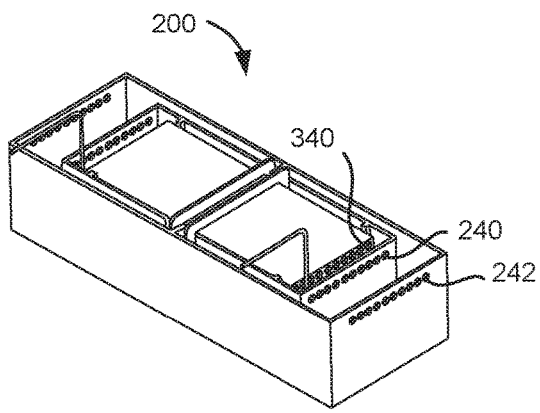
FIGS. 5A, 5B and 5C show three views of a horizontal gel box described herein.
Figure 5B:
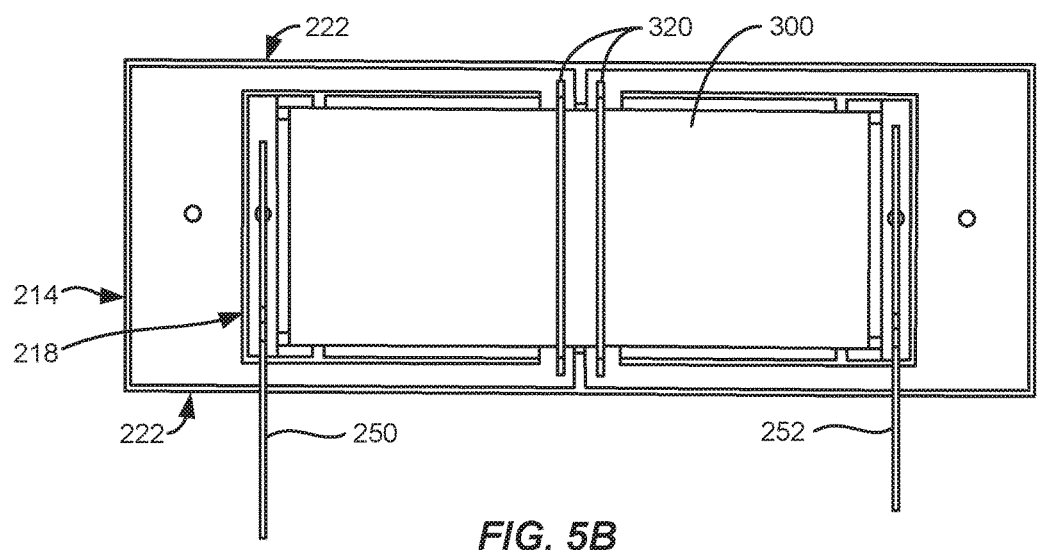
Figure 5C:
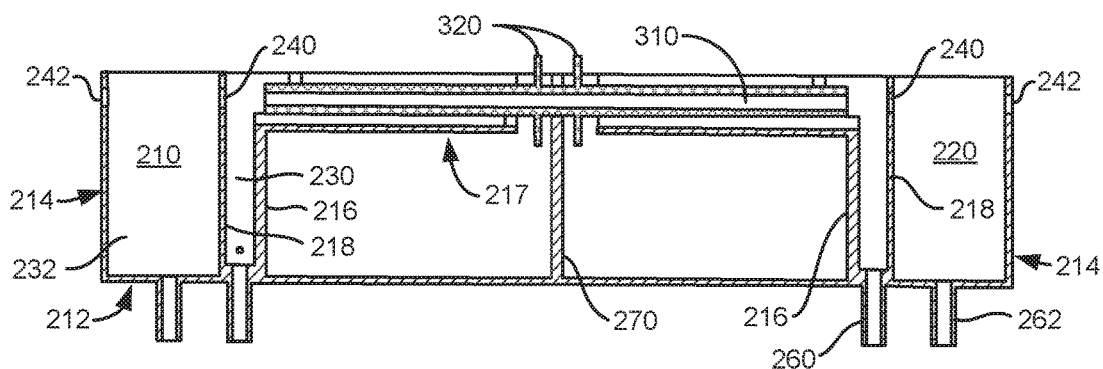

Turning now to FIG. 5, an exemplary, non-limiting embodiment will be described. As shown in FIGS. 5A and 5C, the device (200) comprises first and second chambers (210, 220), each chamber having a floor (212), an outer wall (214), an inner wall (216), and a dividing wall (218). As shown in FIG. 5B, each chamber further comprises two side walls (222) joined to the outer wall (214). The dividing wall (218) separates each chamber into an inner chamber portion (230) and an outer chamber portion (232). The dividing wall further comprises one or more openings (240) located near the top of the dividing wall. In some embodiments, the outer wall comprises one or more openings (242) that are horizontally aligned with the openings (240) of the dividing wall.

Each chamber further comprises an electrode (250, 252) disposed within the inner portion (230). The inner chamber portion (230) comprises an inlet (260) that is in fluid communication with an outlet (262) in the outer chamber portion (232). The inlet (260) and outlet (262) are connected to a pump (not shown) for circulating buffer between the inner and outer chamber portions. In operation, the buffer enters the inlet (260) and flows through the openings (240) in the dividing wall (218) to the outlet (262). However, in some embodiments, the position of the inlet and outlet is reversed, such that outer portion (232) comprises the inlet, and the inner portion (230) comprises the outlet, such that in operation, buffer flows into the outer portion (232), through the openings in the dividing wall, and into the inner portion before exiting via the outlet.

The device (200) can further comprise a removable gel carrier housing (300) comprising two parallel plates separated by a space. The gel housing (300) can contain a gel (310), e.g., a polyacrylamide gel, disposed in the space between the two parallel plates. The gel can be poured or polymerized in the housing by a user, or the housing can come preloaded with a precast gel. The housing (300) is open at each end such that the gel (310) is exposed at each end of the housing. The housing (300) is disposed on top of the inner walls (216) such that the gel material is approximately at the same level as the openings (240) in the dividing wall (218). In some embodiments, the inner walls further comprise a horizontally disposed shelf (217) connected to the top portion of the inner wall and configured to support the gel housing (300). In some embodiments, the housing (300) comprises a plurality of openings (340) at each end that are aligned with the openings (240) in the dividing wall (218). In some embodiments, the device (200) further comprises a vertical wall (270) that fluidically separates the chambers (210, 220). The wall (270) can also provide support for the gel housing. The gel housing or the device can further comprise vertical partitions or dams (320) that prevent buffer from flowing over the top of the housing between the chambers (210, 220).

In operation, samples comprising an analyte of interest are loaded onto one end of the gel, and the gel housing comprising the gel and loaded sample is placed onto the device such that it rests on top of the inner walls (or the shelf), where the ends of the gel are horizontally aligned with the openings (240) in the dividing wall (218). In some embodiments, buffer is circulated into the inner chamber portion of each chamber via the inlet such that buffer fills the inner chamber and contacts the exposed ends of the gel. Excess buffer flows through the openings The dynamic buffer flow provides electrical continuity between the electrodes in each chamber and the gel. Thus, electrical connection between the gel and the electrodes does not rely on a static buffer, which eliminates the need for a physical seal between the gel housing and the buffer reservoirs.

Methods for Extracting a Gel

Also provided herein are methods for extracting a gel from a gel housing. Unlike conventional methods, the methods allow extracting a gel without opening or breaking a seal in the gel housing. Thus, in some embodiments, the method comprises extracting a gel from a housing containing the gel. The housing has open first and second ends, such that the gel is exposed at the first and second end. The gel is contacted at the first end with an extrusion member with sufficient force to push the gel out of the second end of the housing, thereby extracting the gel from the housing.

In some embodiments, the gel and the extrusion member have similar cross-sectional shapes, which allows the extrusion member to apply even force across the exposed surface of the gel. In some embodiments, the gel is a cross-linked gel, e.g., a polyacrylamide gel. In some embodiments, the housing has one or more (e.g., a plurality of) gel electrophoresis channels. The electrophoresis channels have a first end and a second end, and the gel is contacted at the first end of the channel with the extrusion member with sufficient force to push the gel out of the second end of the channel. After the analyte (e.g., a protein) is transferred to the second solid support, one or more characteristics of the analyte can be determined or identified, for example, by contacting the analyte with an antibody using western analysis.

In some embodiments, the gel is extruded onto a first solid support that is porous and comprises ions (e.g., a transfer card or similar solid support as described above). In some embodiments, the extruded gel is exposed to an electric field with sufficient electromotive force to transfer an analyte in the gel to a second solid support (e.g., a membrane).

In some aspects, a method for analyzing an analyte following gel electrophoresis is provided. In some embodiments, the method comprises extruding a gel comprising analytes separated by size or charge from a gel housing, and contacting the extruded gel with an electric field such that analytes are electrophoretically transferred to a solid support. In some embodiments, the gel housing comprises one or more separation channels, and the gel is extruded onto a track aligned with the separation channels. In some embodiments, the gel is extruded from a separation channel of the cassette device as described above onto a solid support comprising tracks aligned with the separation channels. The extruded gel is then contacted with an electric filed between first and second transfer electrodes such that the analytes are electrophoretically transferred to a second solid support. The transferred analytes immobilized on the second solid support can then be analyzed to determine one or more characteristics of the analyte. In some embodiments, the analyte is a protein and the characteristic is determined by western analysis.

In some embodiments, the method comprises vibrating the gel housing to extrude the gel from the housing. The vibrations can be combined with force applied by the slidable gel extrusion members, or used alone to extrude the gel.

In the above embodiments, the gel can be any size or shape that is capable of being extruded from a gel housing. For example, the gel can be a single rectangular slab, multiple smaller slabs, strips having rectangular or trapezoidal cross-section, or cylinders having circular or oval cross sections. The gel can be casted in the housing, or casted in a mold and inserted into the housing prior to electrophoresis. In some embodiments, the gel is a pre-cast gel.

Systems

In some aspects, systems for imaging and/or optically analyzing a gel are provided. The system can be used to detect a dye that is added to the gel to monitor the progress of electrophoresis. In some embodiments, the dye is a small molecular weight dye that migrates faster than analytes in the gel. Following electrophoresis, the gel strips may become slightly shifted or mechanically misaligned relative to each during the extrusion process. The shift may cause errors in determining the molecular weight of analytes in the gel. Thus, the system is useful for detecting shifts in the gel following extrusion, which allows for correction of mechanical shifts after gel extrusion. In some embodiments, the system provides an image of the gel during or after electrophoresis, but before the gel is extruded from the housing. The image can be used to correct for mechanical shifts in the gel strips relative to each after extrusion from the housing or during transfer to the second solid support (e.g., membrane). Imaging systems are well known in the art. One representative imaging system is the ChemiDoc™ Touch Imaging System (BioRad).

In one aspect, the system comprises image processing software. In some embodiments, the software comprises instructions that control an image capturing device. The image capturing device is programed to capture a first image of the gel in the housing prior to extrusion, and to capture a second image of the gel after extrusion, and to detect and correct shifts in alignment of the gel strips relative to each. In some embodiments, the image alignment is corrected by reference to a dye that migrates through the gel. In some embodiments, the image alignment is corrected by reference to a labeled molecular weight ladder that is present in the gel. In some embodiments, the second image is captured after the analytes and the dye in the gel are transferred to a solid support, such as a membrane.

In some embodiments, the system comprises a horizontal gel electrophoresis device described herein, an instrument comprising an image capturing device, and a programmable computer comprising software that controls and/or analyzes the captured image.

In some embodiments, a method for correcting the alignment of analytes in a gel is provided. The method comprises comparing a first image of a gel prior to extrusion to a second image of the gel after extrusion, and determining if a reference band in the first image is shifted relative to the reference band in the second image. If the reference band is shifted, the method corrects the alignment based on the position of the reference band before the gel is extruded.

Computer Implemented Methods and Systems

Any of the methods described herein may be totally or partially performed with a computer system including one or more processors, which can be configured to perform the steps of the methods. Thus, embodiments can be directed to computer systems configured to perform the steps of any of the methods described herein, potentially with different components performing a respective step or a respective group of steps. Although presented as numbered or ordered steps, steps of the methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In some embodiments, the computer implemented method is implemented by a computer system that is in electronic communication with an image scanner that is capable of detecting the bands in a gel or image of a gel. The computer implemented method can detect and correct mechanical shifts in the alignment of gel images before and after extrusion of the gel or gel strips from the gel housing or separation channels.

In some embodiments, the computer implemented method corrects for mechanical shifts using an algorithm. The algorithm is capable of mapping an image of the gel taken after gel extraction from the cassette to a reference image taken prior to extraction. Mapping is created by identifying bands and gel markers within lanes on both images by using image processing functions such as contour search, noise reduction and filtering. Mapping allows re-alignment of the lanes by adding an offset or a linear transformation per lane. The corrected band or marker position allows determining properties of proteins or other molecules that have run in the gel.

In some embodiments, the method to correct misalignment in the gel uses the following algorithm:
1. Acquire two images, the first before extracting the gel (when the gel is in the cassette) and the second after the gel is extracted.
2. Use image processing tools for detecting the lanes, the dye bands and/or additional markers in the gel in both the images. For example, the leading band (bromophenol blue) is detected in each lane.
3. Map the bands and/or markers from the second image to their corresponding band and marker from the first image. This is done for each lane.
4. The algorithm output specifies for each point in the second image its original position in the first image. In addition it creates from the second image a corrected image in which the lanes and bands are moved to their original position before the gel was extracted from the cassette.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein. In some embodiments, the computer product comprises a non-transitory computer readable medium storing a plurality of instructions for controlling a processor to perform an operation of one or more of the following steps:
i) obtaining a first image of a gel before the gel is extruded from the gel housing or separation channel;
ii) obtaining a second image of the gel after the gel is extruded from the housing or separation channel;
iii) comparing the first and second images, and correcting the image of the gel after extrusion based on the image of the gel before extrusion.

In some embodiments, the computer product comprises a non-transitory computer readable medium storing a plurality of instructions for controlling a processor to perform an operation of one or more of the following steps:
i) obtaining a first image of a gel before the gel is extruded from the gel housing or separation channel;
ii) obtaining a second image of the gel after the gel is extruded from the housing or separation channel;
iii) comparing the first and second images, and correcting the image of the gel after extrusion based on the image of the gel before extrusion.

In some embodiments, a system is provided, the system comprising the computer product described above, and one or more processors for executing instructions stored on the computer readable medium.

Figure 6:
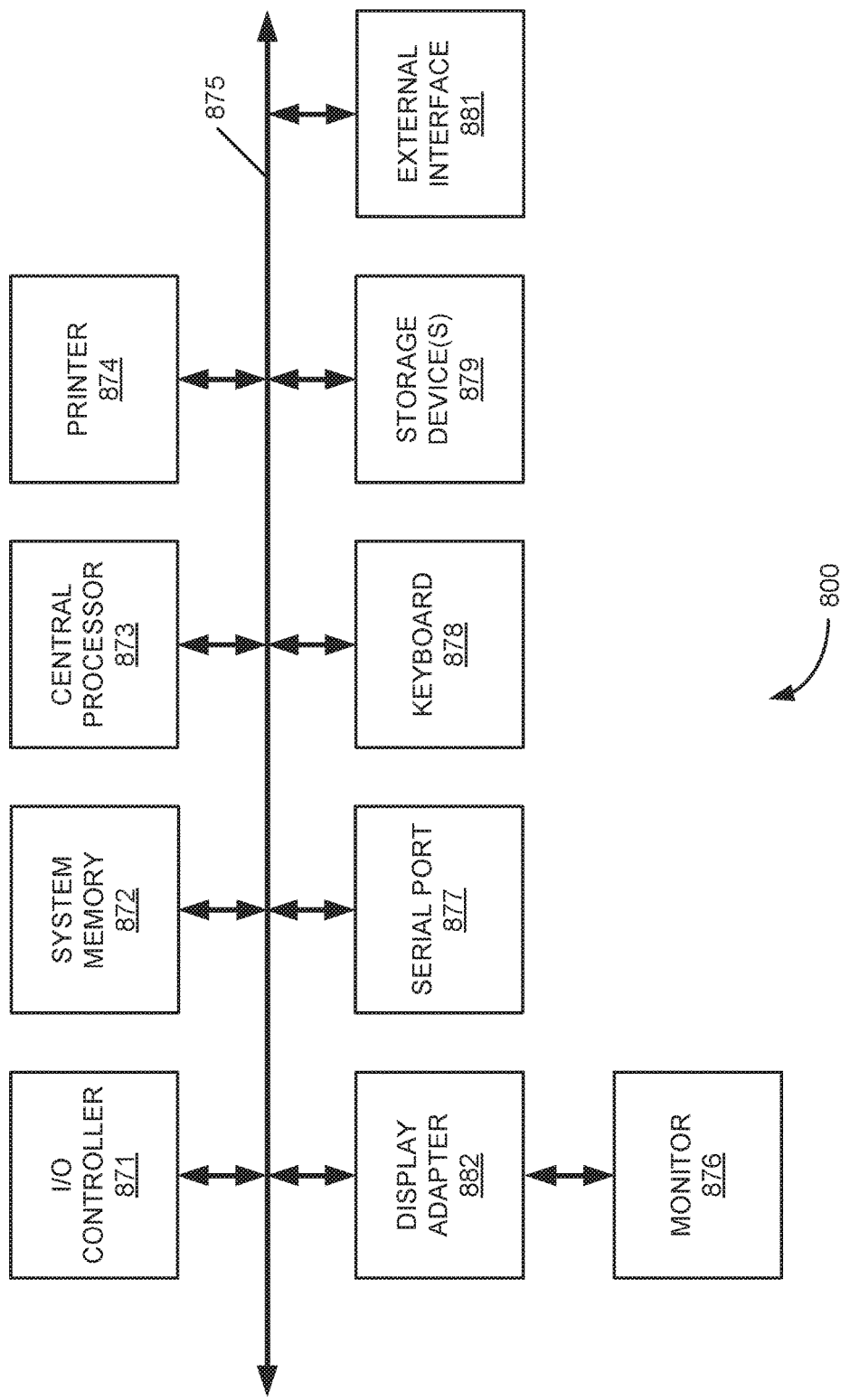
FIG. 6 shows a block diagram of an example computer system 800 usable with the system and methods according to embodiments described herein.

FIG. 6 shows a block diagram of an example computer system 800 usable with system and methods according to embodiments of the present disclosure.

Any of the computer systems mentioned herein may utilize any suitable number of subsystems. Examples of such subsystems are shown in FIG. 6 in computer apparatus 800. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 6 are interconnected via a system bus 875. Additional subsystems such as a printer 874, keyboard 878, storage device(s) 879, monitor 876, which is coupled to display adapter 882, and others are shown. Peripherals and input/output (I/O) devices, which couple to I/O controller 871, can be connected to the computer system by any number of means known in the art, such as serial port 877. For example, serial port 877 or external interface 881 (e.g. Ethernet, Wi-Fi, etc.) can be used to connect computer system 800 to a wide area network such as the Internet, a mouse input device, or a scanner. The interconnection via system bus 875 allows the central processor 873 to communicate with each subsystem and to control the execution of instructions from system memory 872 or the storage device(s) 879 (e.g., a fixed disk, such as a hard drive or optical disk), as well as the exchange of information between subsystems. The system memory 872 and/or the storage device(s) 879 may embody a computer readable medium. Any of the data mentioned herein can be output from one component to another component and can be output to the user.

A computer system can include a plurality of the same components or subsystems, e.g., connected together by external interface 881 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that the embodiments described above can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A device for horizontal electrophoresis, the device comprising:
    a first and second chamber for holding buffer, the first and second chamber separated from each other and each comprising a floor, wherein the floor of the first and second chamber each comprises one or more opening(s) providing fluid communication between the first and second chambers and one or more separation channel(s) comprising an electrophoresis gel;
    the separation channel(s) residing below the floor of the first and second chambers, wherein the separation channel(s) has a first and second end, the first end of said separation channel(s) abutting an extrusion member capable of sliding to extrude the electrophoresis gel in the separation channel out of the second end of the separation channel(s);
    a cathode disposed within the first chamber and an anode disposed within the second chamber; and
    a track aligned with each separation channel to receive the electrophoresis gel extruded by the extrusion member from the separation channel.

2. The device of claim 1, wherein the openings in the floor of at least one of the first and second chambers form sample wells that protrude above a surface of the floor such that a volume of sample can be contained in each well.

3. The device of claim 1, further comprising a first transfer electrode positioned above the track and a second transfer electrode positioned below the track, wherein the track is part of a solid support comprising pores and a medium for conducting ions.

4. The device of claim 1, wherein the floor of the first or second chamber, and/or a bottom and/or a top of the separation channel comprises a transparent material.

5. The device of claim 1, wherein the device comprises a plurality of separation channels.

6. The device of claim 1, wherein the first and second chamber are separated from each other by a dividing wall, or the first and second chamber are horizontally separated from each other such that at least a portion of the separation channel is visible between the first and second chambers.

7. The device of claim 1, wherein the first and/or second chamber further comprises an inlet and an outlet configured to circulate buffer by way of a pump that flows buffer from the inlet to the outlet.

8. A method for analyzing an analyte following gel electrophoresis, the method comprising:
- extruding an electrophoresis gel comprising analytes separated by size or charge from the separation channel of the device of claim 1 onto a track aligned with the separation channel;
- contacting the extruded electrophoresis gel with an electric field between first and second transfer electrodes such that the analytes are electrophoretically transferred to a solid support; and
- analyzing the analyte.

9. The method of claim 8, wherein the electrophoresis gel is extruded by contacting the electrophoresis gel with an extrusion member with sufficient force to push the electrophoresis gel out of the separation channel onto the track.

10. A system for aligning images of an electrophoresis gel, comprising:
- the device of claim 1 wherein the electrophoresis gel comprises a dye band;
- a detector capable of detecting the dye band; and
- a computer configured with executable instructions for aligning a first image of the electrophoresis gel and a second image of the electrophoresis gel,
- wherein the first image is obtained before the electrophoresis gel is extruded from the separation channel(s), and the second image is obtained after the electrophoresis gel is extruded from the separation channel(s), and the images are aligned based on a position of the dye band before the electrophoresis gel is extruded.

11. The device of claim 1, wherein the separation channel(s) are electrically insulated from each other, and are open at each end such that the electrophoresis gel is exposed at both ends of the separation channel.

* * * * *